(12) United States Patent
McRae

(10) Patent No.: US 10,285,840 B2
(45) Date of Patent: May 14, 2019

(54) ANTERIOR CRUCIATE LIGAMENT SUPPORT BAND

(71) Applicant: Scott M. McRae, Owens Crossroads, AL (US)

(72) Inventor: Scott M. McRae, Owens Crossroads, AL (US)

( * ) Notice: Subject to any disclaimer, the term of this patent is extended or adjusted under 35 U.S.C. 154(b) by 503 days.

(21) Appl. No.: 14/862,541

(22) Filed: Sep. 23, 2015

(65) Prior Publication Data

US 2017/0079826 A1 Mar. 23, 2017

(51) Int. Cl.
*A61F 5/00* (2006.01)
*A61F 5/01* (2006.01)

(52) U.S. Cl.
CPC .......... *A61F 5/0106* (2013.01); *A61F 5/0123* (2013.01)

(58) Field of Classification Search
USPC ................. 602/26, 62, 20; D24/190–192
See application file for complete search history.

(56) References Cited

U.S. PATENT DOCUMENTS

| | | | | |
|---|---|---|---|---|
| 3,945,046 A * | 3/1976 | Stromgren | ............ | A61F 13/062 602/63 |
| 4,240,414 A * | 12/1980 | Theisler | ................ | A61F 13/062 602/26 |
| 4,693,241 A * | 9/1987 | Trznadel | ............... | A61F 13/062 602/62 |
| 5,417,647 A * | 5/1995 | Down | .................. | A61F 5/0106 2/16 |
| 5,588,956 A * | 12/1996 | Billotti | .................... | A61F 5/012 128/DIG. 20 |
| 5,624,388 A * | 4/1997 | Lehr | ..................... | A61F 5/0118 602/20 |
| 6,402,712 B1 * | 6/2002 | Gauvry | ................. | A61F 13/062 602/26 |
| 6,520,926 B2 * | 2/2003 | Hall | ......................... | A61F 5/01 602/64 |
| 6,610,023 B2 * | 8/2003 | Steponovich | ......... | A61F 5/0106 128/869 |
| 7,037,286 B1 * | 5/2006 | Reinhardt | ............ | A61F 5/0118 128/878 |
| 7,166,760 B1 * | 1/2007 | Talbot | .................. | A61F 5/0111 602/23 |
| 7,198,610 B2 * | 4/2007 | Ingimundarson | ..... | A61F 5/0123 602/16 |
| 8,608,677 B2 * | 12/2013 | Motyer | ................. | A61F 5/0111 128/878 |
| 9,220,622 B2 * | 12/2015 | Ingimundarson | ..... | A61F 5/0123 |
| D768,956 S * | 10/2016 | Jirsa | .............................. | D2/700 |
| 2002/0010410 A1 * | 1/2002 | Steponovich | ......... | A61F 5/0106 602/26 |

(Continued)

*Primary Examiner* — Kim M Lewis
(74) *Attorney, Agent, or Firm* — George P Kohler

(57) ABSTRACT

An anterior cruciate ligament support band is disclosed that includes an elastic, generally x-shaped body with a pair of diverging upper arms and a pair of diverging lower arms. The respective ends of the upper arms may be fastened to each other and the respective ends of the lower arms may be fastened to each other. The body is placed against the posterior side of the wearer's leg at the knee joint, while the ends of the upper arms are fastened together above the knee joint on the front of the leg and the ends of the lower arms are fastened together below the knee joint on the front of the leg.

17 Claims, 5 Drawing Sheets

(56) References Cited

U.S. PATENT DOCUMENTS

| | | | | |
|---|---|---|---|---|
| 2008/0294079 A1* | 11/2008 | Sterling | ................ | A61F 5/012 |
| | | | | 602/13 |
| 2009/0105622 A1* | 4/2009 | Sterling | ............... | A61F 5/0123 |
| | | | | 602/26 |
| 2010/0210988 A1* | 8/2010 | Dallison | ................ | A61F 5/01 |
| | | | | 602/61 |
| 2011/0098618 A1* | 4/2011 | Fleming | ............... | A61F 5/0123 |
| | | | | 602/16 |
| 2014/0243722 A1* | 8/2014 | Mueller | ............... | A61F 5/0109 |
| | | | | 602/26 |
| 2015/0290013 A1* | 10/2015 | Mueller | ............... | A61F 5/0123 |
| | | | | 602/26 |

* cited by examiner

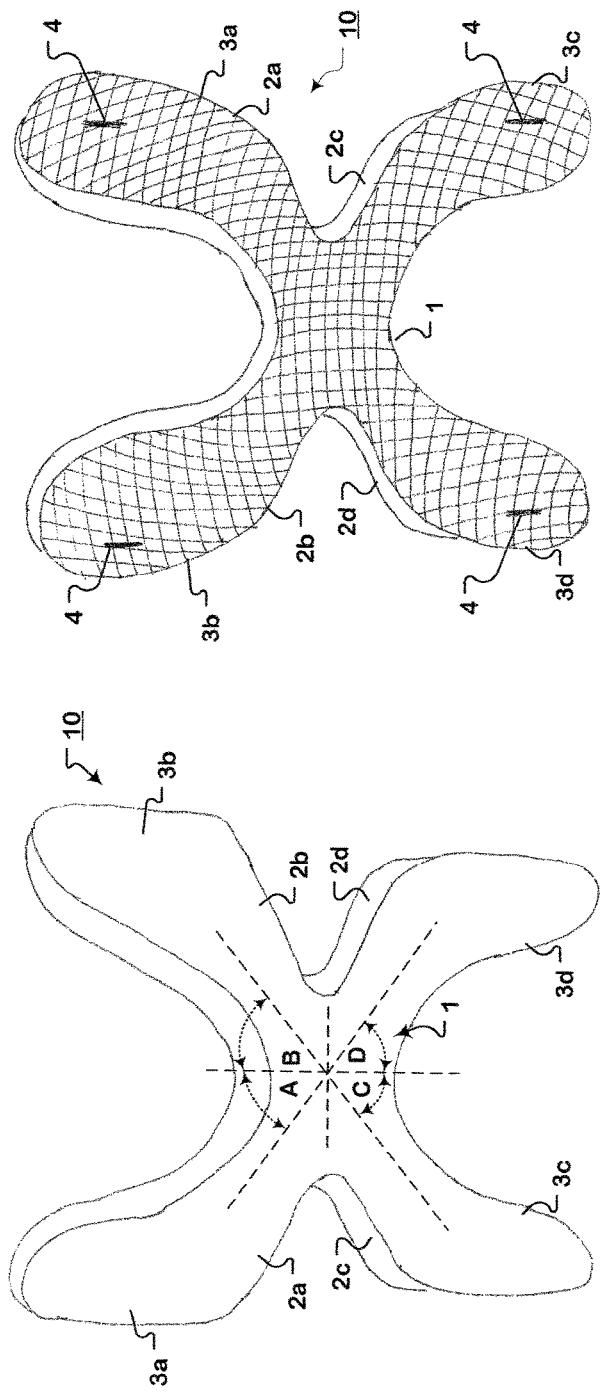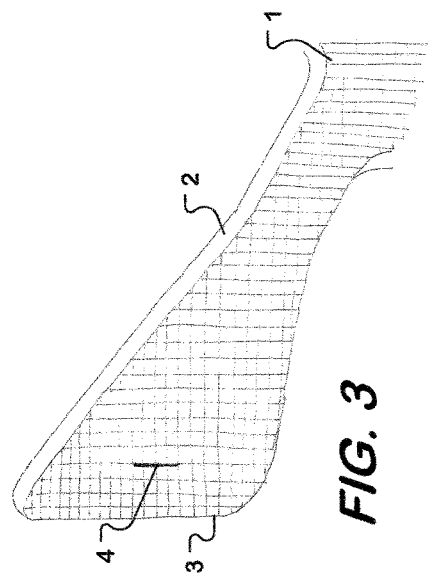

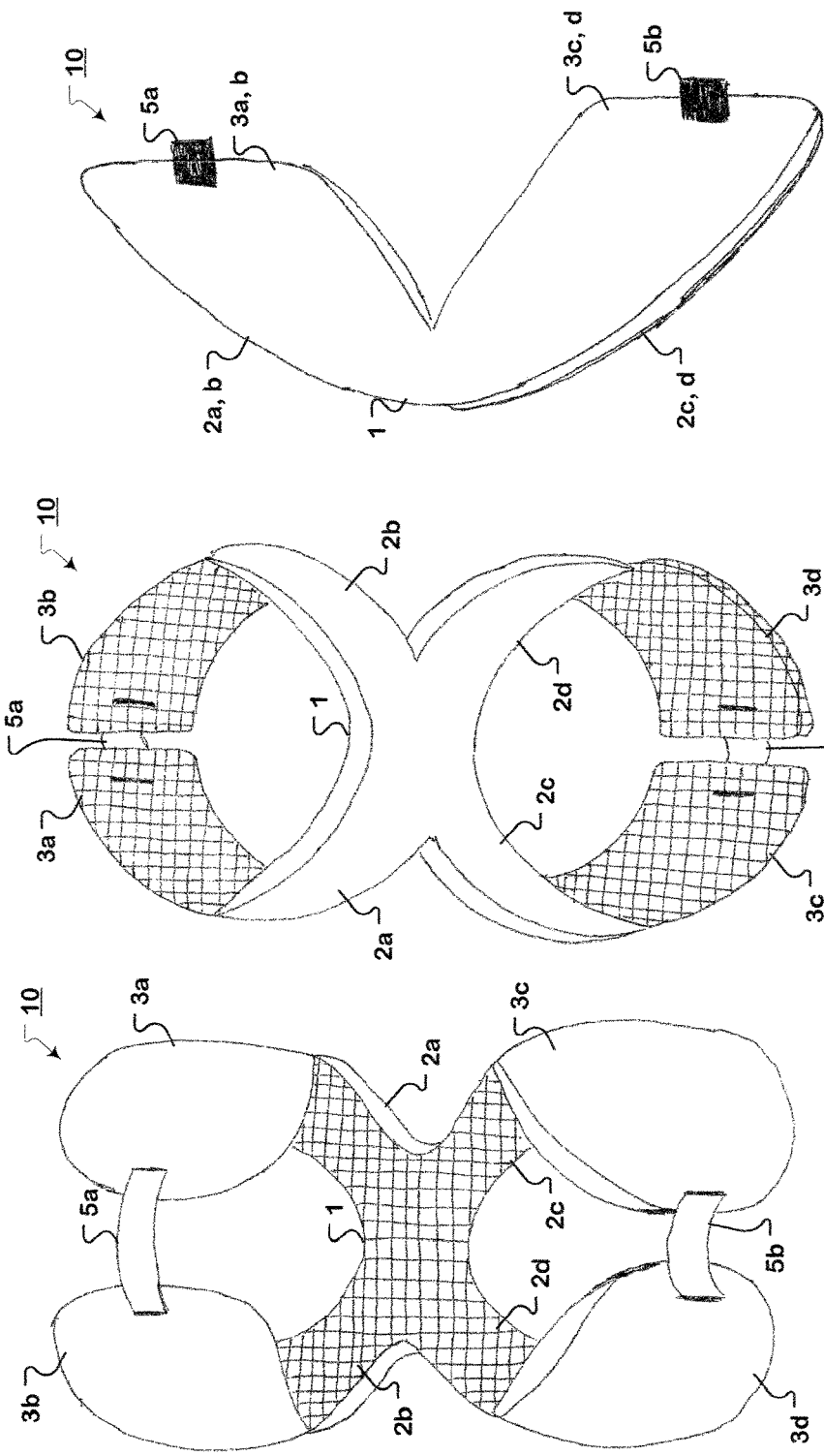

A-A

ANTERIOR CRUCIATE LIGAMENT SUPPORT BAND

BRIEF DESCRIPTION OF THE DRAWINGS

The novel anterior cruciate ligament support band is described with reference to the accompanying drawings. In the drawings, like reference numbers indicate identical or functionally similar elements.

FIG. 1 is a view of the rear side of an exemplary support band;

FIG. 2 is a view of the front side of the support band of FIG. 1;

FIG. 3 is an isolated view of an exemplary arm of the support band of FIG. 1;

FIG. 4 is a front view of an exemplary support band illustrating attachment of corresponding tabs;

FIG. 5 is a rear view of the support band of FIG. 4;

FIG. 6 is a side view of the support band of FIG. 5;

DETAILED DESCRIPTION

Figure 7:
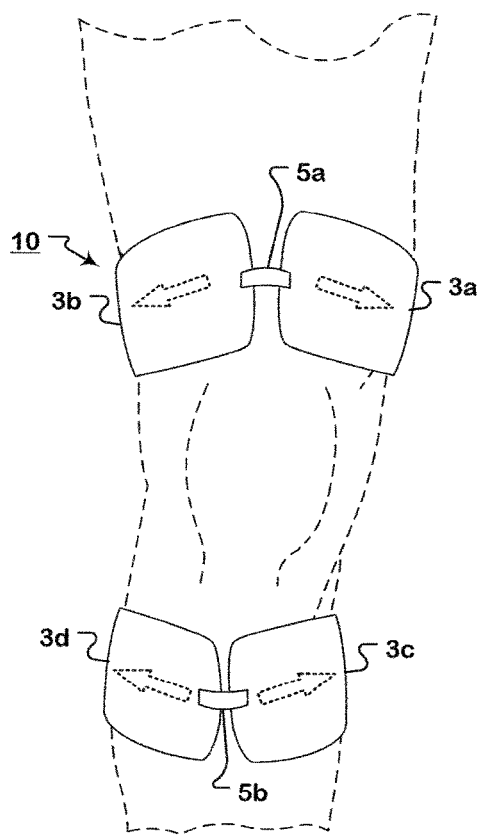
FIG. 7 is a front view depicting a support band wrapped around a user's knee.

The various embodiments of the anterior cruciate ligament support band and their advantages are best understood by referring to FIGS. 1 through 10 of the drawings. The elements of the drawings are not necessarily to scale, emphasis instead being placed upon clearly illustrating the novel features and principles of operation. Throughout the drawings, like numerals are used for like and corresponding parts of the various drawings.

With reference to FIGS. 1 through 3, an exemplary anterior cruciate ligament support band 10 comprises a generally "x"-shaped body 1 with four arm members 2a-d extending laterally away from the center of the body 1 at acute angles A-D. As illustrated, the two upper arm members 2a, b extend laterally upward while the two lower arm members 2c, d extend laterally downward. The ends 3a-d of the arms 2a-d transition to roughly vertical tabs, and, one embodiment, each end 3a-d may comprise a generally vertical slit 4 defined therethrough.

Figure 8:
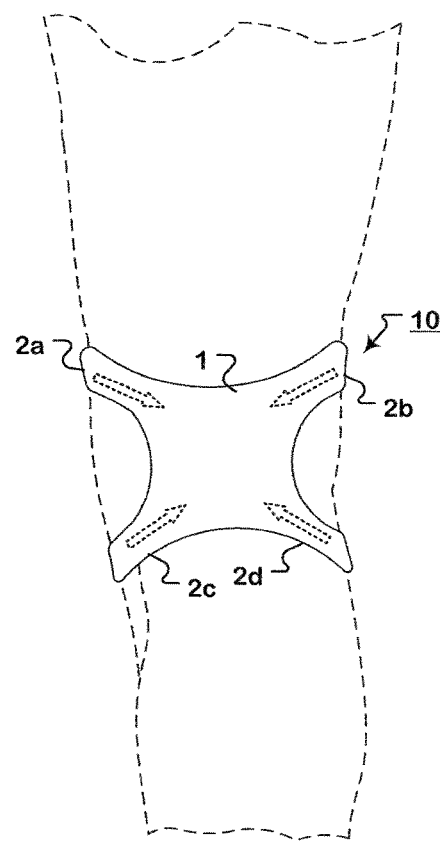
FIG. 8 is a rear view depicting a support band wrapped around a user's knee.

In such an embodiment, slits 4 provide attachment points for upper and lower fastening strips 5a, 5b as shown in FIGS. 4 through 6. Accordingly, the two upper arms 2a, b are drawn together at their respective ends 3a, b and removably fastened together with the upper fastening strip 5a. Likewise, the lower arms 2c, d are drawn together and attached at their respective ends 3c, d by the lower fastening strip 5b. FIGS. 7 and 8 depict the band 10 on a wearer. It should be noted that ends 3a-d may be attached as described by a variety of fasteners. To this end, fastening strips 5a, 5b may be of a hook-and-loop type fastener, e.g., Velcro®. Alternatively, fastening may be accomplished with snaps, hooks, ties, buckles, buttons, and other suitable fasteners known in the art or hereafter developed.

The anterior cruciate ligament support band 10 is formed of any suitable, flexible, resilient, elastic material, for example, from a sheet of neoprene with a nylon outer casing and an inner nylon lining. In one embodiment the support band 10 is integrally formed from a silicone-based elastomer, for example, medical-grade silicone rubber. The elastomer should be tear-resistant with a relatively high tensile strength and durability, as well as hypo-allergenic to reduce the likelihood of skin reactions. An example of such material is sold by Nusil Technology, LLC, of Carpenteria, Calif.

Other suitable materials with which to form the band 10 include natural and synthetic rubbers, foams, thermoplastic elastomers, polyurethane elastomers, polyvinyl chloride (PVC) elastomers, olefinic elastomers, polyamide elastomers, and the like. In addition, certain gelatinous elastomers which are substantially non-flowable at room temperature (below 130 degrees Fahrenheit) may be used. Such gels are disclosed in U.S. Pat. No. 5,994,450 which is hereby incorporated by reference. Alternative gels, which the inventor considers inferior due to their high tack, excessive oil bleed and low durability, have been patented in the name of John Y. Chen of Applied Elastomerics, Inc. Examples of such gels may be found in U.S. Pat. Nos. 6,161,555; 6,148,830; 6,117,176; 6,050,871; 6,033,283; 5,962,572; 5,938,499; 5,884,639; 5,868,597; 5,760,117; 5,655,947; 5,633,286; 5,624,294; 5,508,334; 5,475,890; 5,336,708; 5,334,222; 5,324,222; 5,262,468; 5,260,371; 5,239,723; 5,153,254; 4,618,213; and 4,369,284. U.S. Pat. No. 5,994,450 is believed to be the first to disclose a styrene ethylene-butylene ethylene-propylene styrene gel, and U.S. Pat. No. 3,827,999 by inventor Ronald Crossland appears to be the first to disclose an SEBS gel. Another gel that is available is called "J-SOFT", a pelleted injection molding material offered by ATP, a division of Newgrange Company in Rhode Island.

Additionally, the support band 10 may be fabricated using an A-B-A tri block copolymer plasticized with a plasticizing agent such as an oil. Some embodiments of the A-B-A triblock copolymer will have glassy end blocks and elastomer mid blocks. For example, SEEPS, SEBS, and SEPS are such polymers, and mineral oil is a suitable plasticizing agent. Additives may be included such as anti-oxidants, colorants, and microspheres to reduce weight and/or tackiness. It is expected that the ratio of oil to polymer in the gel will be in the range of 1.0:1.0 to 8.5:1.0, although it could be outside of that range. In most gel structures of the invention, the ratio of oil to polymer will be 1.5:1.0 to 5.5:1.0.

Those skilled in the relevant arts will appreciate that the body 1 should be relatively resistant to flex, but still be sufficiently pliable to accommodate bending of the wearer's knee while having a "shape memory" characteristic. With this in mind, gelatinous elastomers are a good choice as a material for because of their ability to be formed into a shape that has durability and flexibility that can be subject to repeated or sustained loads without a permanent change in material dimensions or properties and due to their ability to reshape hydrostatically under load.

The band 10 is donned by placing the front surface of the body 1 against the posterior side of the wearer's knee joint (FIG. 8). The upper arms 2a, b are drawn around the leg and their respective ends 3a, b are removably fastened to each other on the anterior side of the leg just above the knee joint. Similarly, the lower arms 2c, d are drawn around the leg and their respective ends 3c, d are fastened to each other on the anterior side of the leg just below the knee joint. Preferably, the anterior surface of the support band is tacky such that it removably adheres to the wearer's skin, especially the skin above and below the anterior, lateral and medial sides of the knee. Thus, because of the elasticity of the band 10 material, a force, indicated by the dashed arrows, is exerted on the wearer's anterior, lateral and medial knee soft tissue toward the central area of the body 1 of the band 10 and the posterior side of the leg.

Figure 9:
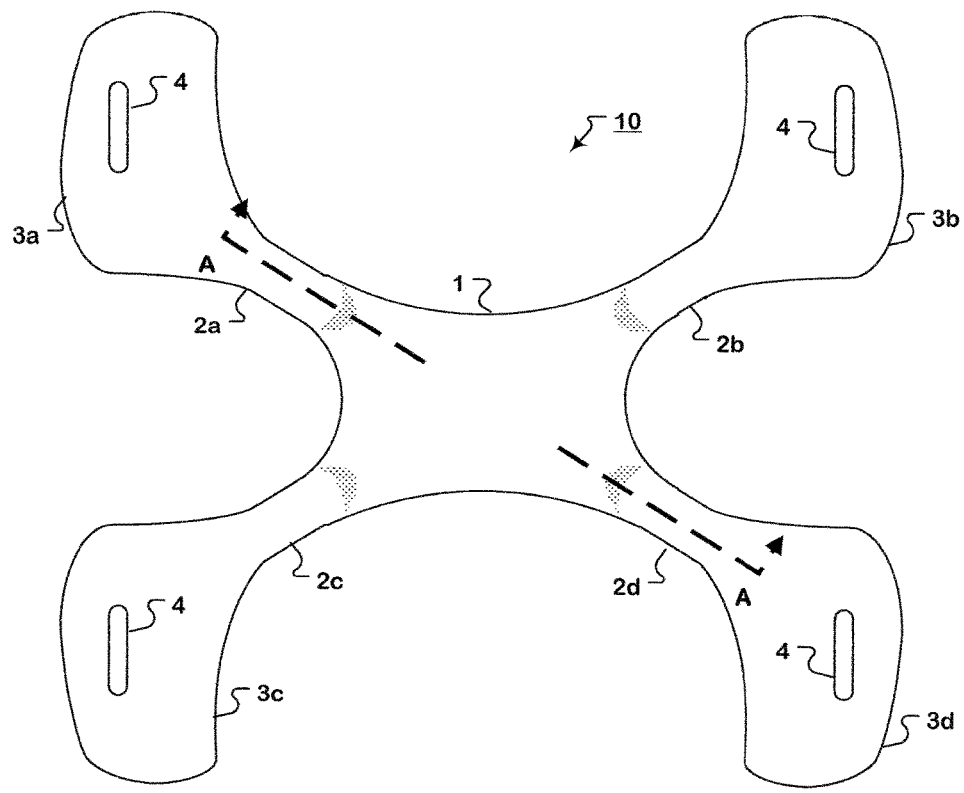
FIG. 9 is a rear view of another exemplary embodiment of an anterior cruciate ligament support band.
Figure 9A:
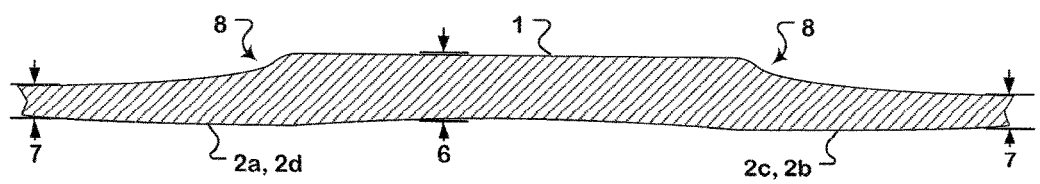
FIG. 9A is a fragmentary section view of the embodiment shown in FIG. 9 along line A-A.

FIGS. 9 & 9A depict a further embodiment of the anterior cruciate ligament support band 10 in which the body 1 comprises a thickness 6 that is greater than thickness 7 of the arms 2a-d. In an embodiment in which the support band 10 comprises a gelatinous elastomer, added thickness to the body 1 section provides added support and resistance to flexing. By way of example, only the thickness of the body 1 could be between 9 and 18 mm while the arm 2 thickness 7 may be between 5 to 10 mm. As shown in FIG. 9A, a transition region 8 is interposed between the body 1 and the arms 2 to promote a continuous decrease in thickness from that of the body 1 to that of the arms 2. In this embodiment, it will be appreciated that the body 1 may exhibit less elasticity that the arms 2.

Figure 10:
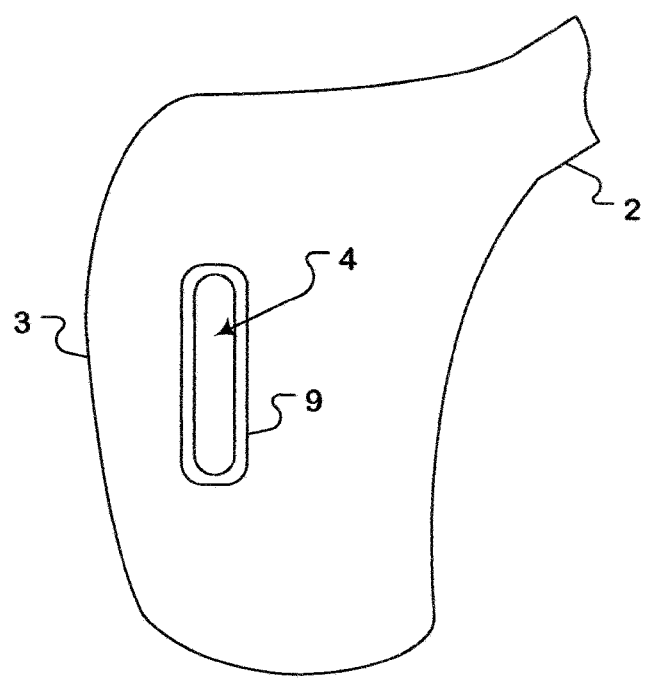
FIG. 10 is an isolated view of an arm according to another exemplary embodiment.

With reference now to FIG. 10, in a further embodiment, slit 4 is surrounded by a grommet 9 that helps to prevent the slit 4 from opening further and tearing through the ends 3. Grommet 9 may be comprised of suitable metal or plastic. It will also be appreciated that the support band 10 may include a layer of fabric adhered to either front or rear surfaces of the band 10, or both.

As described above and shown in the associated drawings, the present invention comprises an anterior cruciate ligament support band. While particular embodiments have been described, it will be understood, however, that any invention appertaining to the support band described is not limited thereto, since modifications may be made by those skilled in the art, particularly in light of the foregoing teachings. It is, therefore, contemplated by the appended claims to cover any such modifications that incorporate those features or those improvements that embody the spirit and scope of the invention.

What is claimed is:

1. An anterior cruciate ligament rapport band consisting of:
   an elastic, generally x-shaped body;
   first and second elastic tipper arms integrally formed in one piece with said body and extending laterally away therefrom at inclining acute angles with respect thereto, said first and second elastic upper arms having first and second upper ends, said first and second upper ends having means for fastening said upper ends to each other; and
   first and second elastic lower arms integrally formed in one piece with said elastic, generally x-shaped body and extending laterally away therefrom at declining acute angles with respect thereto, said first and second lower arms having first and second lower ends, said first and second elastic lower ends having means for fastening said lower ends to each other; and
   wherein said elastic, generally x-shaped body is adapted to be placed against a posterior side of a wearer's knee, the upper arms are adapted to be placed to be wrapped around the wearer's leg and fastened together on an anterior side above the knee joint, and the lower arms are adapted to be wrapped around the wearer's leg and fastened together on the anterior side below the knee joint.

2. The anterior cruciate ligament support band of claim 1, further comprising one of a natural rubber, a synthetic rubber, silicone-based elastomer and a gelatinous elastomer.

3. The anterior cruciate ligament support band of claim 2, further comprising an anterior surface adapted to be placed against said wearer's skin, said anterior surface being removably adherent to said wearer's skin.

4. The anterior cruciate ligament support band of claim 1, further comprising a silicone-based elastomer.

5. The anterior cruciate ligament support band of claim 4, further comprising an anterior surface adapted to be placed against said wearer's skin, said anterior surface being removably adherent to said wearer's skin.

6. The anterior cruciate ligament support band of claim 4, further comprising a medical grade silicone rubber.

7. The anterior cruciate ligament support band of claim 1, wherein said body comprises a first thickness and each of said arms comprise a second thickness and wherein said first thickness is greater than said second thickness.

8. The anterior cruciate ligament support band of claim 7, wherein said first thickness is between 9 and 18 mm.

9. The anterior cruciate ligament support band of claim 8, wherein said second thickness is between 5 to 10 mm.

10. The anterior cruciate ligament support band of claim 1, further comprising:
    first and second upper slits defined in said first and second upper ends;
    first and second lower slits defined in said first and second lower ends;
    an upper fastening strip inserted through said first and second upper slits for fastening said first and second upper ends to each other; and
    a lower fastening strip inserted through said first and second upper slits for fastening said first and second upper ends to each other.

11. The anterior cruciate ligament support band of claim 10, wherein each of said slits comprise a grommet.

12. The anterior cruciate ligament support band of claim 1, wherein said fastening means comprises at least one of snaps, hooks, ties, buckles, and buttons.

13. An anterior cruciate ligament support band consisting of:
    a unitary, generally x-shaped elastic member having a body and a pair of integrally-formed upper arms extending therefrom and a pair of integrally-formed lower arms extending therefrom, said body configured to be worn against the posterior side of a wearer's knee joint, said upper arms having fastening means for removably fastening respective upper ends thereof to each other on an anterior aide of the wearer's leg above the knee joint, said lower arms having fastening means for removably fastening respective lower ends thereof to each other on the anterior side of the wearer's leg below the knee joint, said elastic member having an anterior surface adapted to be placed against said wearer's skin, said anterior surface being removably adherent to said wearer's skin.

14. The anterior cruciate ligament support band of claim 13, wherein said fastening means comprises at least one of a hook-and-loop fastener, snaps, hooks, ties, buckles, and buttons.

15. An anterior cruciate ligament support band consisting of an a unitary elastic generally x-shaped elastic member configured to be worn wrapped around a wearer's leg and having upper ends fastened to each other above an anterior side of the wearer's knee joint and lower ends fastened to each other below the anterior side of the wearer's knee joint such that tension in the x-shaped elastic member imparts a pulling force on the wearer's skin toward the posterior of the wearer's leg.

16. The anterior cruciate ligament support band of claim 15, further comprising a silicone elastomer.

17. The anterior cruciate ligament support band of claim 15, further comprising a gelatinous elastomer.

\* \* \* \* \*